United States Patent [19]

Fries et al.

[11] Patent Number: 5,595,618
[45] Date of Patent: Jan. 21, 1997

[54] ASSEMBLY PROCESS FOR A LAMINATED TAPE

[75] Inventors: Donald M. Fries, Combined Locks; Lorry F. Sallee, Pine River, both of Wis.

[73] Assignee: Kimberly-Clark Corporation, Neenah, Wis.

[21] Appl. No.: 415,383

[22] Filed: Apr. 3, 1995

[51] Int. Cl.$^6$ ............................ A61F 13/60; A61F 13/62; B32B 31/18
[52] U.S. Cl. .......................... 156/164; 156/259; 156/265; 156/271; 156/324
[58] Field of Search ..................................... 156/271, 259, 156/256, 324, 264, 265, 164; 604/389, 390

[56] References Cited

U.S. PATENT DOCUMENTS

| | | | |
|---|---|---|---|
| 2,714,889 | 8/1955 | Chambers | 128/287 |
| 3,616,114 | 10/1971 | Hamaguchi | 161/39 |
| 3,867,940 | 2/1975 | Mesek et al. | 128/287 |
| 3,901,236 | 8/1975 | Assarsson et al. | 128/284 |
| 4,050,462 | 9/1977 | Woon et al. | 128/287 |
| 4,051,853 | 10/1977 | Egan, Jr. | 128/287 |

(List continued on next page.)

FOREIGN PATENT DOCUMENTS

| | | |
|---|---|---|
| 011001A1 | 6/1984 | European Pat. Off. . |
| 0191355A1 | 8/1986 | European Pat. Off. . |
| 0217032A3 | 4/1987 | European Pat. Off. . |
| 0233704B1 | 8/1987 | European Pat. Off. . |
| 0339461B1 | 11/1989 | European Pat. Off. . |
| 0379850A1 | 8/1990 | European Pat. Off. . |

(List continued on next page.)

Primary Examiner—Michael W. Ball
Assistant Examiner—Sam Chuan Yao
Attorney, Agent, or Firm—Paul Yee

[57] ABSTRACT

A distinctive method and apparatus provide a technique for forming a fastener system. Generally stated, the apparatus includes a supply mechanism for providing along a machine-direction a first web of material having a medial portion thereof. A first assembly mechanism attaches a second web of material to the medial region of the first web along the machine direction to provide a web laminate, and a first parting mechanism separates the web laminate into at least a first laminate section and a second laminate section. Each laminate section includes a portion of the first web and a portion of the second web, and each laminate section has an edge region thereof. A directing mechanism spaces apart the first and second laminate sections, and a delivery mechanism locates a securement web of fastening material between the first and second laminate sections. The securement web has a first side region and a second side region thereof. A second assembly mechanism affixes the edge region of the first laminate section to the first side region of the securement web, and affixes the edge region of the second laminate section to the second side region of the securement web to thereby form a composite base web which has a media, portion thereof. A second parting mechanism divides the composite web along its medial portion to form at least a first composite securement web and a second composite securement web.

19 Claims, 5 Drawing Sheets

U.S. PATENT DOCUMENTS

| | | | |
|---|---|---|---|
| 4,055,182 | 10/1977 | Mack | 128/287 |
| 4,066,081 | 1/1978 | Schaar | 128/287 |
| 4,076,663 | 2/1978 | Masuda et al. | 260/17.4 GC |
| 4,237,890 | 12/1980 | Laplanche | 128/287 |
| 4,286,082 | 8/1981 | Tsubakimoto et al. | 526/240 |
| 4,522,853 | 6/1985 | Szoon et al. | 428/40 |
| 4,568,344 | 2/1986 | Suzuki et al. | 604/389 |
| 4,585,447 | 4/1986 | Karami | 604/385 A |
| 4,585,448 | 4/1986 | Enloe | 604/378 |
| 4,610,685 | 9/1986 | Raley | 604/366 |
| 4,643,729 | 2/1987 | Laplanche | 604/389 |
| 4,663,220 | 5/1987 | Wisneski et al. | 428/221 |
| 4,699,823 | 10/1987 | Kallenberger et al. | 428/219 |
| 4,704,116 | 11/1987 | Enloe | 604/385 A |
| 4,726,971 | 2/1988 | Pape et al. | 428/40 |
| 4,753,646 | 6/1988 | Enloe | 604/385 R |
| 4,753,649 | 6/1988 | Pazdernik | 604/389 |
| 4,778,701 | 10/1988 | Pape et al. | 428/40 |
| 4,787,897 | 11/1988 | Torimae et al. | 604/389 |
| 4,795,456 | 1/1989 | Borgers et al. | 604/390 |
| 4,801,480 | 1/1989 | Panza et al. | 428/40 |
| 4,826,499 | 5/1989 | Ahr | 604/389 |
| 4,857,067 | 8/1989 | Wood et al. | 604/389 |
| 4,911,702 | 3/1990 | O'Leary et al. | 604/389 |
| 4,916,005 | 4/1990 | Lippert et al. | 428/192 |
| 4,938,753 | 7/1990 | Van Gompel et al. | 604/385.2 |
| 4,978,570 | 12/1990 | Heyn et al. | 428/231 |
| 5,024,672 | 6/1991 | Widlund | 604/390 |
| 5,032,119 | 7/1991 | Hookano | 604/385.1 |
| 5,034,007 | 7/1991 | Igaue et al. | 604/365 |
| 5,057,097 | 10/1991 | Gesp | 604/389 |
| 5,092,862 | 3/1992 | Muckenfuhs et al. | 604/385.2 |
| 5,110,386 | 5/1992 | Ochi et al. | 156/204 |
| 5,170,505 | 12/1992 | Rohrer | 2/69 |
| 5,176,670 | 1/1993 | Roessler et al. | 640/391 |
| 5,176,672 | 1/1993 | Bruemmer et al. | 604/385.1 |
| 5,192,606 | 3/1993 | Proxmire et al. | 428/284 |
| 5,226,992 | 7/1993 | Morman | 156/62.4 |
| 5,312,387 | 5/1994 | Rossini et al. | 604/389 |
| 5,358,500 | 10/1994 | Lavon et al. | 604/385.2 |
| 5,370,634 | 12/1994 | Ando et al. | 604/385.1 |
| 5,399,219 | 3/1995 | Roessler et al. | 156/271 X |

FOREIGN PATENT DOCUMENTS

| | | |
|---|---|---|
| 0396050A2 | 11/1990 | European Pat. Off. . |
| 04333951A2 | 6/1991 | European Pat. Off. . |
| 0463276A1 | 1/1992 | European Pat. Off. . |
| 0487758A1 | 6/1992 | European Pat. Off. . |
| 0532035A3 | 3/1993 | European Pat. Off. . |
| 0532034A2 | 3/1993 | European Pat. Off. . |
| 0539032A1 | 4/1993 | European Pat. Off. . |
| 1359810 | 3/1964 | France . |
| 2403036 | 4/1979 | France . |
| 2606257 | 5/1988 | France . |
| 3419623A1 | 11/1985 | Germany . |
| 3419621A1 | 11/1985 | Germany . |
| 069653 | 4/1986 | Israel . |
| 5-65321 | 8/1993 | Japan . |
| H6-11725 | 2/1994 | Japan . |
| 450816 | 7/1936 | United Kingdom . |
| 990600 | 4/1965 | United Kingdom . |
| 2185383A | 7/1987 | United Kingdom . |
| 2244422A | 12/1991 | United Kingdom . |
| 2257895A | 1/1993 | United Kingdom . |
| WO90/07426 | 7/1990 | WIPO . |
| WO91/00720 | 1/1991 | WIPO . |

ASSEMBLY PROCESS FOR A LAMINATED TAPE

FIELD OF THE INVENTION

The present invention relates to a technique for forming a fastening system. More particularly, the invention relates to a technique for forming an article having a fastening system which incorporates a side panel member connected to a fastener tab.

BACKGROUND OF THE INVENTION

Conventional absorbent articles, such as disposable diapers, have been constructed with elasticized waistbands. Particular article designs have incorporated a stretchable outer cover composed of an elastomeric web material, such as a stretch bonded laminate which includes a layer of nonwoven fabric. Other conventional designs have included elastomeric or nonelastomeric side panel members connected to the lateral side edges of an outercover composed of a polymer film material, and fasteners and fastening tabs have been connected to the side panels for securing the article on a wearer. The fastener tabs have typically been folded into a storage position, and lines of relative weakness, such as score lines, have been employed to direct the location of the fold.

Conventional techniques for forming articles which have fastening systems with panel members, however, have exhibited significant shortcomings when incorporated into high speed manufacturing operations. For example, it has been difficult to provide a reliable technique which consistently folds the fastener tab along the desired fold line and places the folded portion in the appointed storage position. It has also been difficult to consistently fold the fastener tabs without introducing undesired stress concentrations or areas of localized weakness that can lead to a fracturing and breaking away of the fastener tab. As a result, there has been a continued need for an improved manufacturing technique which can more effectively produce an article having a stronger and more reliable fastening system.

BRIEF DESCRIPTION OF THE INVENTION

An apparatus aspect of the invention provides a distinctive device for forming a fastener system. Generally stated, the apparatus includes a supply means for providing along a machine-direction a first web of material having a medial portion thereof. A first assembly means attaches a second web of material to the medial region of the first web along the machine direction to provide a web laminate, and a first parting means separates the web laminate into at least a first laminate section and a second laminate section. Each laminate section includes a portion of the first web and a portion of the second web, and each laminate section has an edge region thereof. A directing means spaces apart the first and second laminate sections, and a delivery means locates a securement web of fastening material between the first and second laminate sections. The securement web has a first side region and a second side region thereof. A second assembly means affixes the edge region of the first laminate section to the first side region of the securement web, and affixes the edge region of the second laminate section to the second side region of the securement web to thereby form a composite base web which has a medial portion thereof. A second parting means divides the composite web along its medial portion to form at least a first composite securement web and a second composite securement web.

A process aspect of the invention can further provide a method for forming a fastener system. The method includes the steps of providing along a machine-direction a first web of material having a medial portion thereof, and attaching a second web of material to the medial portion of the first web along the machine direction to provide a web laminate. The web laminate is separated into at least a first laminate section and a second laminate section. Each laminate section includes a portion of the first web and a portion of the second web, and each laminate section has an edge region thereof. The first and second laminate sections are spaced apart, and a securement web is located between the first and second laminate sections. The securement web has a first side region and a second side region thereof. The edge region of the first laminate section is affixed to the first side region of the securement web, and the edge region of the second laminate section is affixed to the second side region of the securement web to thereby form a composite base web which has a medial portion thereof. The composite web is divided along its medial portion to form at least a first composite securement web and a second composite securement web.

The various aspects of the article of the invention can advantageously provide an improved technique for forming a fastener system in which the fastener tab can be more consistently folded along a desired fold line, and in which the folded portion can be more efficiently placed in its appointed storage position. With the technique, the fastener tab can be more effectively and efficiently folded without incorporating steps which can introduce undesired areas of localized weakness and can lead to a fracturing and breaking away of the fastener tab. As a result, the present invention, in its various configurations, can provide an improved technique for forming an article having a stronger and more reliable fastening system. The resultant article and fastening system can have more consistent quality and can provide more dependable performance.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The method and apparatus of the present invention will be described herein in relationship to their use in producing a fastener system for absorbent articles, particularly disposable absorbent articles. Such articles can be placed against or in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as caps, gowns, drapes, covers, adult incontinence garments, sanitary napkins, children's training pants, and the like.

In particular arrangements, the present invention can advantageously be employed to more efficiently produce a fastening system for incorporation into an absorbent article, such as a disposable diaper having a front waistband section, a rear waistband section and an intermediate section which interconnects the front and rear waistband sections. The article includes a backsheet layer, and a liquid permeable topsheet layer which is superposed on the backsheet layer. An absorbent body is located between the backsheet layer and the topsheet layer, and a fastening system is connected to the article at each laterally opposed end region of at least one of the front and rear waistband sections. Each fastening system can include a side panel member, and the side panels can optionally be constructed to be elastically stretchable at least along a lateral, cross-direction of the article. A fastening tab for securing the article on a wearer is connected to each of the side panels.

Articles which include elastomeric side panels and selectively configured fastener tabs are described in U.S. patent application Ser. No. 168,615 of T. Roessler et al., entitled DYNAMIC FITTING DIAPER, and filed Dec. 16, 1993 (Attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (Attorney docket No. 11,186); and in U.S. patent application Ser. No. 286,086 of D. Fries, entitled A PROCESS FOR ASSEMBLING ELASTICIZED EAR PORTIONS and filed Aug. 3, 1994 (Attorney docket No. 11,169). The disclosures of the above-described documents are incorporated herein by reference in a manner that is consistent (not in conflict) herewith.

Figure 1:
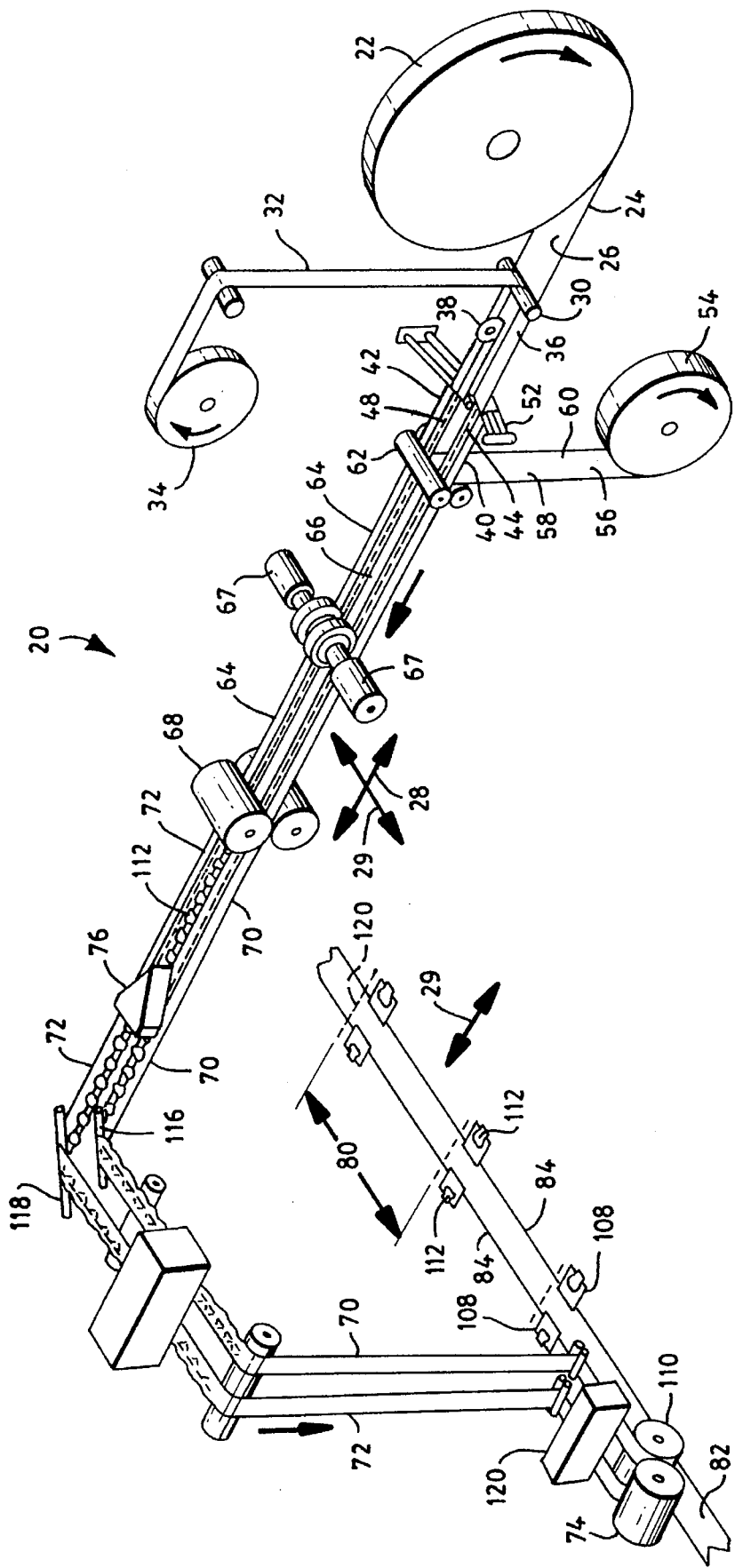
FIG. 1 representatively shows a schematic, perspective view of a method and apparatus of the invention.

The method and apparatus of the invention provide a distinctive technique for forming a fastener system. The invention can further provide a distinctive technique for forming a selected article, such as an elasticized disposable diaper which includes a fastening system. With reference to FIG. 1, a method and apparatus of the invention, shown generally at 20, for forming a fastener system includes a first supplying means, such as a first web roll 22, for providing along a machine-direction 28 a panel web 24 of panel material having a medial portion 26 thereof. A first assembly means, such as assembly rollers 30, attach a second web 32 of material to the medial portion 26 of the first web 24 along the machine direction to provide a web laminate 36. A first parting means, such as cutter 38, separates the web laminate 36 into at least a first laminate section, such as first web section 40, and a second laminate web section, such as second web section 42. Each laminate section 40 and 42 includes a portion of the first web 24 and a portion of the second web 32, and each laminate section has an edge region thereof, such as the inboard edge regions 44 and 48, respectively. A directing means, such as a system of spreader bars 52, spaces apart the first and second laminate sections 40 and 42. A delivery means, such as a system including web supply roll 54 and directing roller 55, locates a securement web 56 between the first and second laminate sections 40 and 42. The securement web has a first side region 58 and a second side region 60 thereof. A second assembly means, such as a system of assembly rollers 62, affixes the edge region 44 of the first laminate section 40 to the first side region 58 of the securement web 56, and affixes the edge region 48 of the second laminate section 42 to the second side region 60 of the securement web to thereby form a composite base web 64 which has a medial portion 66 thereof. A second parting means, such as provided by a second cutting system 68, divides the composite web 64 along its medial portion 66 to form at least a first composite securement web 70 and a second composite securement web 72.

The representatively shown method and apparatus generally has a machine-direction 28 and cross-direction 29. At any particular, selected location along the method and apparatus, the machine-direction is the generally lengthwise direction along which a particular web (or composite web) of material is moving or transported through the process. The cross-direction extends generally along the plane of the web of material, and is perpendicular to the particular machine-direction established by the method or apparatus at the selected location.

Figure 2:
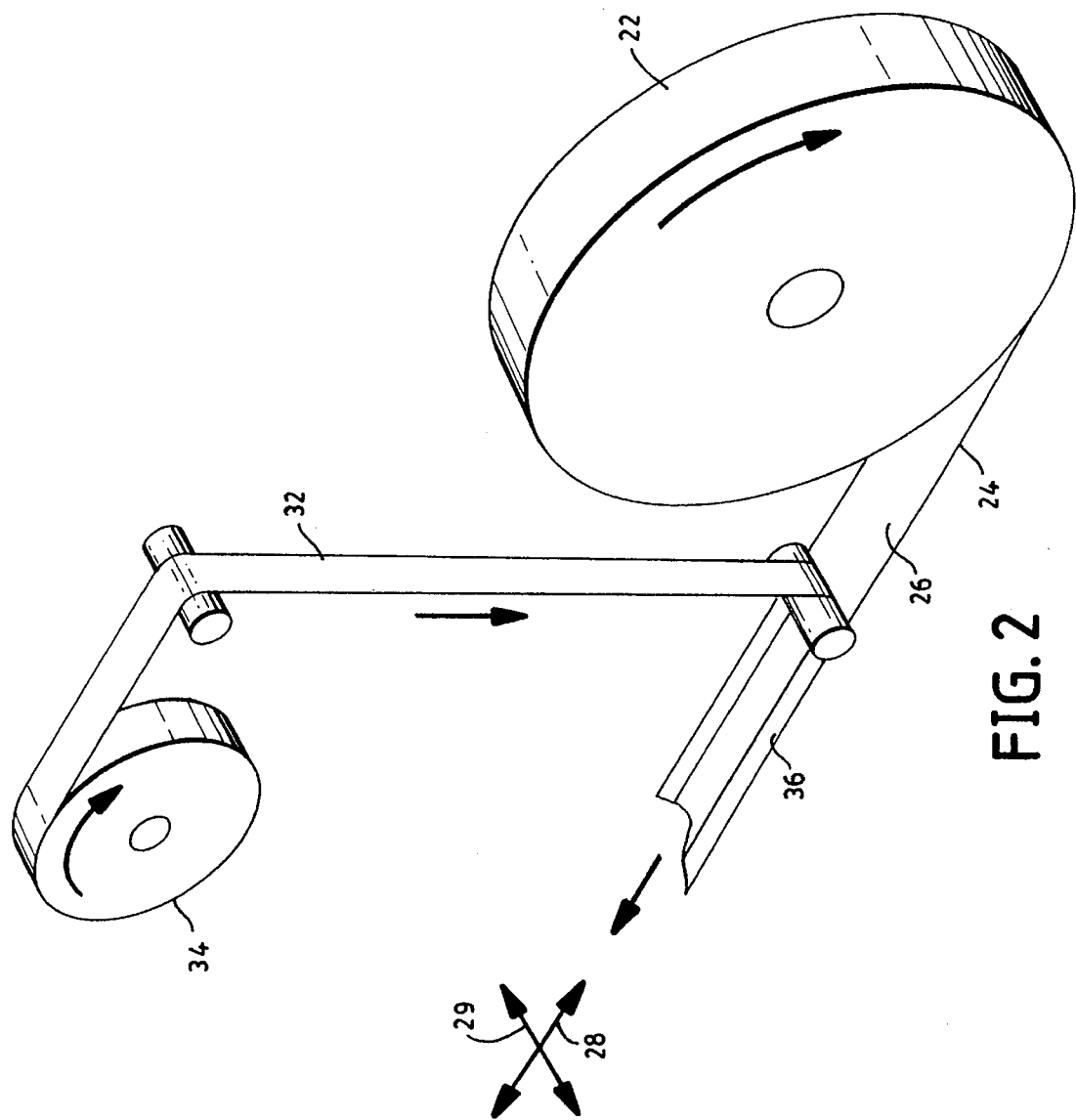
FIG. 2 representatively shows an enlarged view of a portion of the invention which includes the mechanisms for providing the panel web and for laminating the panel web to the reinforcement web.

With reference to FIGS. 1 and 2, a supplying means, such as supply roll 22, provides a first, panel web 24 composed of a selected panel material. The panel material may be substantially nonelastomeric or may be elastomeric. In particular configurations of the invention, the side panel material is composed of an elastomeric material which is elastically stretchable at least along the cross-direction 29 of the panel web 24. The panel material can, for example, be a stretch-bonded-laminate (SBL) material, a neck-bonded-laminate (NBL) material, an elastomeric film, an elastomeric foam material, or the like. For example, suitable meltblown elastomeric fibrous webs for forming panel web 24 are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent application EP No. 0 110 010 published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to M. Mormon, the disclosure of which is hereby incorporated by reference. A particular neck-bonded-laminate (NBL) can be composed of a film of elastomer material sandwiched between two layers of spunbond material. The film can be composed of a KRATON® elastomer available from Shell Oil Company, and the spunbond layers can be composed of spunbond, polypropylene fibers.

A second supplying means, such as supply roll 34, supplies a second, reinforcement web 32, and the reinforcement web is composed of any suitable reinforcement material. For example, the shown embodiment of the reinforcement web 32 can be composed of a web of release tape, and the release tape can include a substrate composed of a polymer film, such as a polypropylene film. Suitable release tape materials are available from Avery Corp., a business having offices located in Painesville, Ohio.

Figure 5:
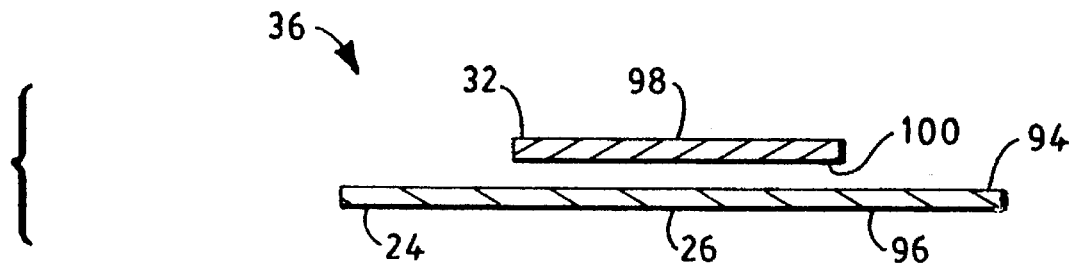
FIG. 5 representatively shows an expanded, schematic cross-sectional view of the web laminate formed by the invention.

Accordingly, the reinforcement web 32 can be a release tape having a release surface 98 and an oppositely located attachment surface 100, as representatively shown in FIG. 5. A suitable release material, which has a limited low level adhesion to conventional pressure-sensitive adhesives, is positioned over the release surface 98, and a suitable attachment mechanism, such as a layer of construction adhesive, is distributed over the attachment surface 100. The construction adhesive is employed to affix the reinforcement web 32 onto an appointed section of the final article. As representatively shown, the panel web 24 has a first major facing surface 94 and a second major facing surface 96, and the release tape web can be operably bonded and laminated to the medial portion 26 of the first surface 94 of the panel web to provide the web laminate 36. Desirably the reinforcement web 32 is substantially centered along the cross-direction of the panel web 24. The resultant assembly provides a composite web laminate 36 in which the release-coated surfaces of the release tapes are in a generally exposed position. The web laminate 36 is then operably directed and transported for further processing.

Figure 3:
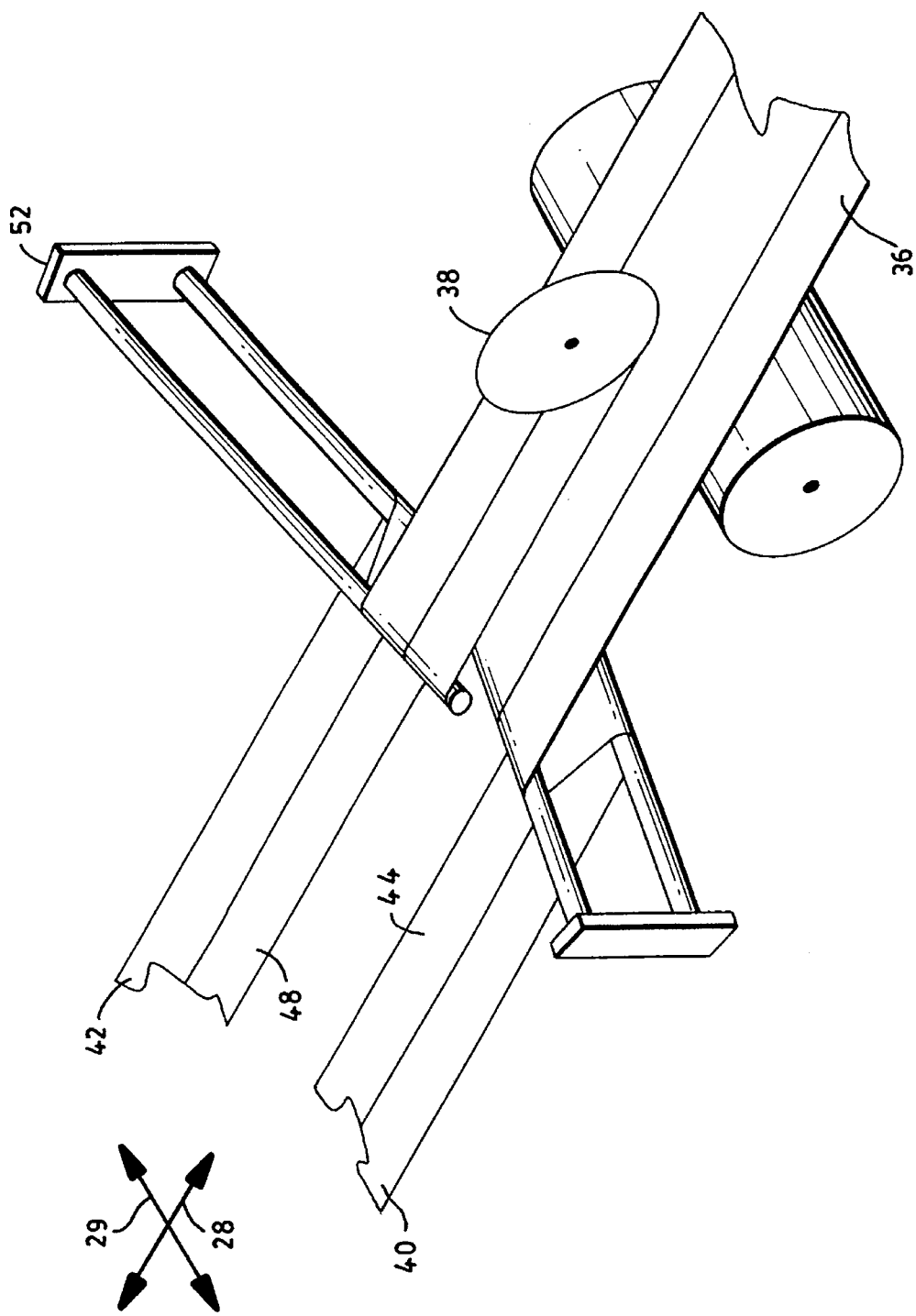
FIG. 3 representatively shows an enlarged view of a portion of the invention which includes the mechanisms for dividing the web laminate into first and second laminate sections, and for spacing apart the laminate sections.

With reference to FIGS. 1 and 3, a suitable separating mechanism, such as a slitter or other cutter 38, is employed to divide the web laminate 36 into a first laminate section 40 and a second laminate section 42. In the illustrated configuration, for example, slitter 82 can separate the laminate web 36 into first and second laminate sections which have substantially equal cross-directional widths. Optionally, the separated laminate section webs 40 and 42 can have unequal cross-directional widths, as desired.

The relative positioning of the first and second laminate sections 40 and 42 is adjusted to a desired spacing along the cross-deckle direction 29 of the process by an operable directing means, such as provided by a spreader mechanism 52. In the illustrated embodiment, for example, the spreader mechanism can include a conventional system of turn bars which reposition and relocate the first and second webs of side panel material at a desired spacing therebetween. In particular, the spreader mechanism 52 can include a first pair of turn bars which are tilted and canted in a manner well known to the art to produce the desired repositioning of the first laminate section 40. The first laminate section 40 moves in an S-shaped path to pass over its first, top turn bar and then pass back and under its second, bottom turn bar to become offset by a predetermined distance away from second laminate section 42.

Similarly, a conventional second set of turn bars are tilted and canted at appropriate angles in a manner well known in the art to reposition the second laminate section 42. In particular, the second laminate section moves in another S-shaped path to pass over its first, top turn bar and then pass back and under its second, bottom turn bar in a manner which directs a second laminate section 42 to a position that is spaced the desired distance away from first laminate section 40. After the spreader mechanism has generated the desired lateral, cross-directional spacing between the first laminate section 40 and the second laminate section 42, the two laminate sections are directed to a second assembling means, such as provided by a system of assembly rollers 62.

Figure 4:
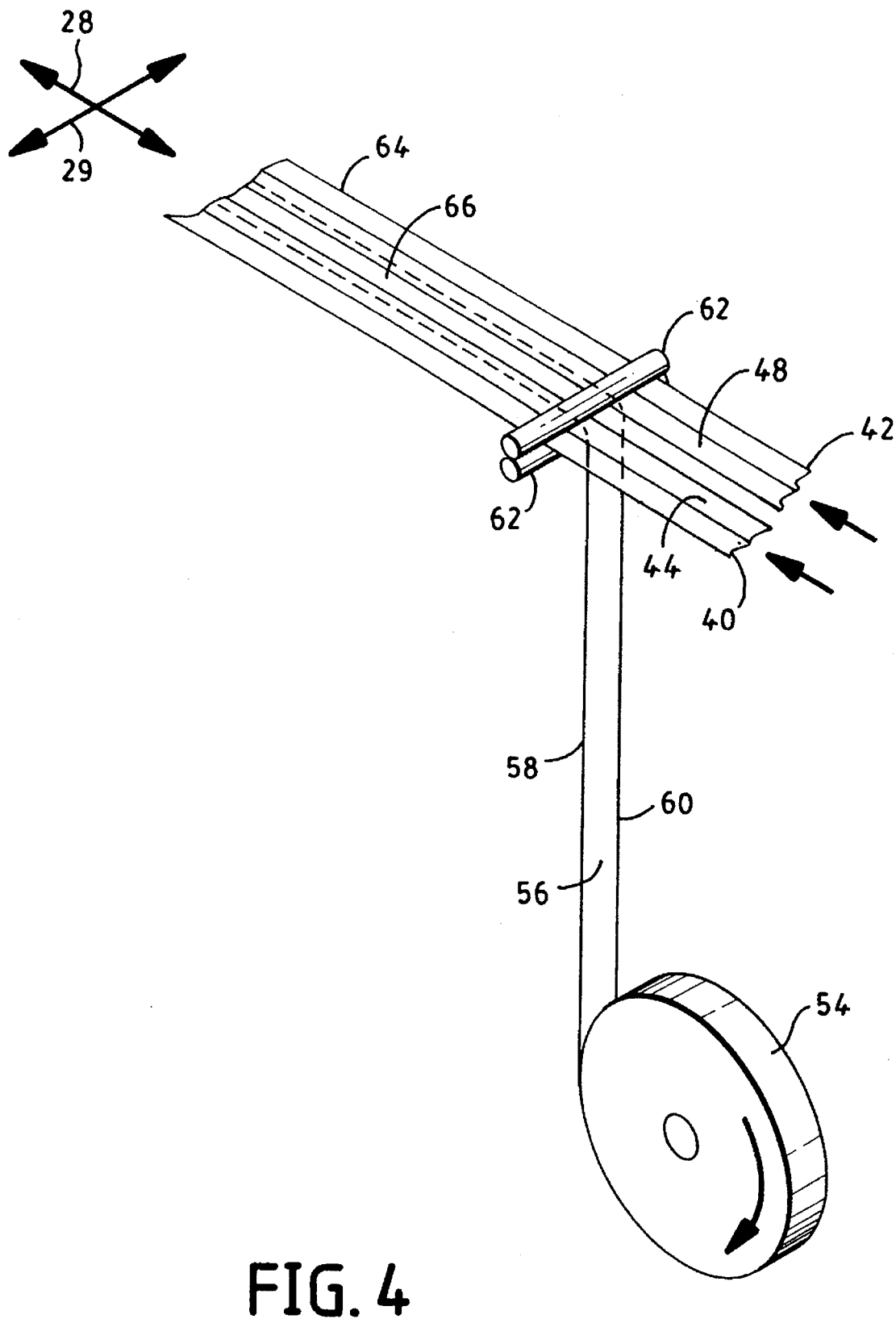
FIG. 4 representatively shows an enlarged view of a portion of the invention which includes the mechanisms for delivering the securement web and for mating the securement web to the spaced apart laminate sections.

With reference to FIGS. 1 and 4, a delivering means, such as a supply roll 54, supplies a securement web 56 composed of fastener substrate material. The securement web has first and second side edge regions 58 and 60 which are oppositely positioned with respect to the cross-deckle direction of the securement web. The securement web 56 is operably guided and directed into the assembly rollers 62, and is interposed between the first and second laminate sections 40 and 42 to allow an operable interconnection between the laminate sections and the securement web 56 to form a composite base web 64. In particular, the side edge region 44 of the first laminate section 40 can be overlapped and affixed to the first side region 58 of the securement web 56. Similarly, the side edge region 48 of the second laminate section 42 can be overlapped and affixed to the second side region 60 of the securement web 56.

The securement web may be composed of various substrate materials. For example, the shown embodiment of the securement web can be composed of a polymer film, such as a polypropylene film. Suitable film materials are available from Avery Corp., a business having offices located in Painesville, Ohio. Alternatively, the securement web may be composed of a woven or nonwoven fabric, such as a spunbonded nonwoven fabric.

Figure 6:
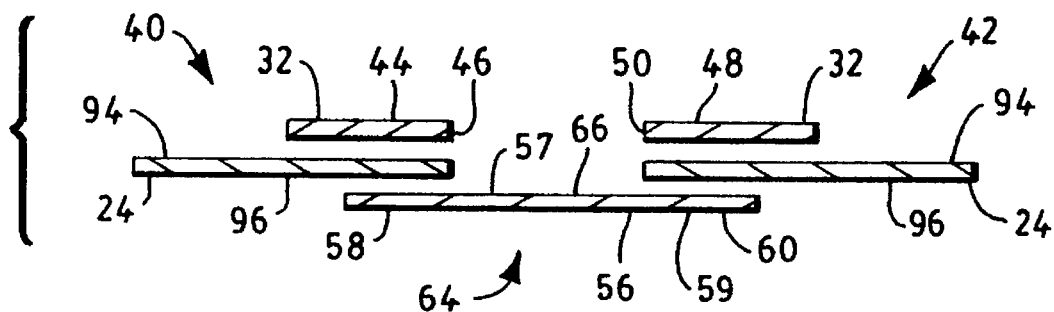
FIG. 6 representatively shows an expanded, schematic cross-sectional view of the composite base web formed by the invention.

With reference to FIG. 6, the shown embodiment of securement web 56 includes a securement surface 57, a user surface 59, and laterally opposed side regions 58 and 60. A suitable securing means is positioned onto the securement surface 57 of the securement web. In the shown configuration, the securing means is provided by a layer of primary adhesive distributed over the securing surface, and the securement web provides a web of adhesive tape material. Alternatively, the securing means may be provided by a cohesive material, and optionally, the securing means may be provided by operably attaching a cooperating component of a interengaging, mechanical fastener. For example, the securing means may include a hook component or loop component of a hook-and-loop fastener system.

Where the securement web is an adhesive tape web, the layer of primary adhesive can be employed to operably affix the side regions 58 and 60 of the securement web to the appointed edge regions 44 and 48 of the web laminate sections 40 and 42, respectively. Alternatively, other types of connecting means, such as thermal bonds, sonic bonds, mechanical stitching, stapling, and the like or combinations thereof, may be employed to permanently attach the securement web to the laminate sections. For example, in the shown arrangement, a rotary ultrasonic bonding mechanism 67 is employed to provide supplemental bonding.

In the illustrated composite base web 64, the securement surface 57 of the web 56 connects to the second surface 96 of the portion of the panel web 24 which is employed to form each of the laminate web sections 40 and 42. The first laminate web section 40 includes an inboard edge region 44, and the edge region includes a terminal edge 46. Similarly, the second laminate web section 42 includes an inboard edge region 48, and the edge region includes a terminal inboard edge 50. At the terminal edge 46 and 50 of each of the laminate sections, the reinforcement web material 32 is substantially coterminous with the panel web material 24.

The composite base web 64 is operably directed into a second separating means, such as a die cutting system 68, to longitudinally divide the composite web into a pair of composite fastener webs 70 and 72. The cutter produces an undulating, serpentine division line which is positioned along a medial section 66 of the composite base web 64. The serpentine line extends generally along the machine-directional, length dimension of the composite web 64 and includes alternately traversing, side-to-side sections thereof. The traversing sections of the dividing line can include retroceding portions thereof to provide for distinctively shaped fastening tabs 112, and with regard to the fastener tabs, the material of the securement web 56 provides a fastener tab substrate. The traversing sections of the serpentine line can also extend into the reinforcement web material located on each of the laminate section webs 40 and 42 to optionally form finger tab regions positioned at the distal, free ends of each of the fastener tabs. Additional details regarding the construction of suitable fastening tabs and fastening system are found in the above-described U.S. patent application Ser. No. 168,615 of T. Roessler et al., entitled "DYNAMIC FITTING DIAPER" and filed Dec. 16, 1993.

In the shown configuration of the invention, the composite fastener webs 70 and 72 are operably directed to a system of conventional folding boards 76 to reposition the individual fastening tabs 112 into a storage position against an appointed surface of its associated fastener web 70 or 72, as desired. Where the reinforcement web 32 is composed of a release tape and securement web 56 is composed of a substrate bearing a layer of primary securement adhesive thereon, for example, the folding operation can place the primary adhesive of the fastening tabs 112 into contact with the release surface 98 of the release tape for storage.

Figure 7:
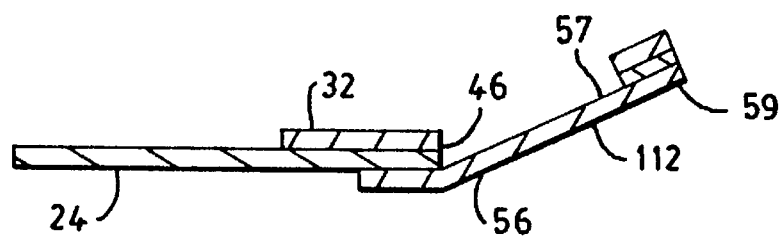
FIG. 7 representatively shows a schematic, cross-sectional view of a partially folded fastener tab.

Thus, when the securement web 56 is interconnected between the first and second laminate sections 40 and 42, the terminal edges 46 and 50 of each laminate section can advantageously induce a stress concentration in the securement web along each of the terminal edges 46 and 50 when the fastener tabs 112 are folded by the folding boards 76. As representatively shown in FIG. 7, the discrete stress concentration along the terminal edges 46 and 50 can more reliably define a desired fold line without the use of conventional weakening procedures, such as scoring. As a result, the invention can provide a more reliable folding operation while maintaining the strength and reliability of the individual fastening tabs 112.

A phase adjusting means, such as provided by alignment turn bars 116 and 118, operably everts the fastener webs 70 and 72, and repositions the lengthwise, machine-directional phasing of the fastener tabs on first fastener web 70 relative to the fastener tabs on second fastener web 72. In the everting operation, the fastener webs 70 and 72 are laterally flipped and reversed such that the fastening tabs 112 are shifted from being located along the inboard edge regions of the fastener webs and are moved to become located along the outboard edge regions of the fastener webs. The additional repositioning, phasing operation is configured to operably arrange appointed, corresponding pairs of fastening tabs 112 into a substantial cross-deckle alignment along the cross-direction of the process and apparatus. Accordingly, the process and apparatus provide at least one corresponding, laterally opposed pair of fasteners, which includes a first fastener tab from the first composite fastener web 70 and a second fastener tab from the second composite fastener web 72. In the illustrated embodiment, the process is advantageously constructed to provide a serial multiplicity of corresponding, laterally opposed pairs of the first and second fasteners.

The substantially aligned first and second fastener webs 70 and 72 can be prepared for further attachment to other components of the desired article. In the illustrated configuration, for example, the composite fastener webs 70 and 72 are directed to an applicator 120 which deposits a suitable adhesive onto the regions of the fastener webs that are appointed for further attachment. Other attaching mechanisms, such as thermal bonds, sonic bonds and the like may also be employed to supplement or replace the described adhesive attachment.

In further aspects of the method and apparatus of the invention, the first and second fastener webs 70 and 72 are directed to a suitable third separating mechanism, such as a rotary cutter 74, for partitioning along the cross-direction of the webs to form a plurality of individual fastener systems 108. The individual fastener systems are directed to a suitable construction assembling mechanism, such as a mechanism including assembly roller 110, which can be configured to attach individual fastener systems onto a major body-facing side or outward-facing side of an article web 82, as desired.

In particular, the assembly mechanism affixes the individual fastener systems 108 to opposed sides 84 and 86 of the article web 82, and opposed pairs of the individual fastener systems 108 are substantially aligned along the cross-direction 29 of the article web 82. The article web can then be separated into a plurality of individual articles by conventional separating means.

For example, a phased, cut-and-place, intermittent assembling means, such as a mechanism comprising a conventional vacuum slip roll 110 and a rotary knife and anvil system 74, can be employed to connect opposed, cross-directionally aligned pairs of the fastener systems 108 to laterally opposite side regions 84 of the article web 82. In the illustrated embodiment, for example, the cut-and-place assembling mechanism is constructed and arranged to operably connect a sequential plurality of the paired fastener systems 108 to the article web at a plurality of predetermined, spaced-apart locations along the machine-direction of the article web 82. An example of a suitable arrangement of rotary cutter and vacuum slip roll is described in U.S. Pat. No. 4,795,510 issued Jan. 3, 1989 to M. Wittrock et al. and entitled "PROCESS FOR APPLYING REINFORCING MATERIAL TO A DIAPER COVER MATERIAL" (Attorney docket No. 8366), the disclosure of which is hereby incorporated by reference in a manner that is consistent herewith.

The resultant article web 82 can be constructed to define an interconnected plurality of individual article segments 80, and a conventional cutting mechanism (not shown) can then separate the article web 82 along preselected division lines 120 to produce selected individual articles. The separating step can be performed by employing any conventional cutting mechanism, such as a rotary cutter or the like.

The invention can further include mechanisms for providing a web of backsheet material, and for positioning at least one absorbent body at a selected location along a machine directional length of the backsheet web. A plurality of absorbent bodies can, for example, be positioned at predetermined, regularly spaced locations along the length of the backsheet web. Another mechanism can then deliver a web of topsheet material to sandwich the absorbent body between the web of backsheet material and the web of topsheet material.

Other aspects of the invention can include a mechanism for attaching at least a pair of lengthwise extending elasticized containment flaps to the bodyside surface of the topsheet web. Suitable containment flap configurations are described in detail in U.S. Pat. No. 4,704,116 issued Nov. 11, 1987 to K. Enloe and entitled DIAPERS WITH ELASTICIZED SIDE POCKET, the disclosure of which is hereby incorporated by reference in a manner that is consistent herewith. Other containment flap configurations are described in U.S. patent application Ser. No. 208,816 of R. Everett et al., entitled ABSORBENT ARTICLE HAVING AN IMPROVED SURGE MANAGEMENT and filed Mar. 4, 1994 (Attorney docket No. 11,375), the disclosure of which is hereby incorporated by reference in a manner that is consistent herewith.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A method for forming a fastener system, comprising the steps of:

(a) providing along a machine-direction a first web of material having a medial portion thereof;

(b) attaching a second web of release material to said medial portion of said first web along said machine-direction to provide a web laminate;

(c) separating said web laminate into at least a first laminate section and a second laminate section, each laminate section including a portion of said first web and a portion of said second web of release material, and each laminate section having an edge region thereof;

(d) spacing apart said first and second laminate sections;

(e) locating a securement web between said first and second laminate sections, said securement web having a first side region a second side region, and a securing means on a securing surface of the securement web;

(f) affixing said edge region of said first laminate section to said first side region of said securement web, and affixing said edge region of said second laminate section to said second side region of said securement web to thereby form a composite base web which has a medial portion thereof;

(g) dividing said composite web along its medial portion to form at least a first composite securement web and a second composite securement web.

2. A method as recited in claim 1, further comprising the step of:

(h) sectioning said first and second composite securement webs to provide a plurality of individual fastener systems.

3. A method as recited in claim 1, wherein said providing step (a) includes the step of providing said first web in a form which is elastically stretchable.

4. A method as recited in claim 1, wherein said dividing step (g) includes the step of dividing said composite web along a serpentine line which extends into each of said first and second laminate sections.

5. A method as recited in claim 1, wherein
said locating step (e) includes the step of providing said securement web in a form which includes an adhesive fastening material on a major facing surface of said securement web.

6. A method as recited in claim 1, wherein said locating step (e) includes the step of providing said securement web with a component of a hook-and-loop fastening system on a major facing surface of said securement web.

7. A method as recited in claim 1, wherein said locating step (e) includes the step of providing said securement web in a form which includes a hook component of a hook-and-loop fastening system on a major facing surface of said securement web.

8. A method as recited in claim 1, wherein said locating step (e) includes the step of providing said securement web in a form which includes a loop component of a hook-and-loop fastening system on a major facing surface of said securement web.

9. A method as recited in claim 2, further comprising the step of (i) folding said first and second composite securement webs to provide first and second folded composite webs.

10. A method as recited in claim 2, further comprising the steps of:

(j) affixing said individual fasteners to opposed sides of an article web, (k) substantially aligning opposed pairs of said individual fasteners along a cross-direction of said article web, and (l) separating said article web into a plurality of individual articles.

11. An apparatus for forming a fastener system, comprising:

a first supplying means for providing along a machine-direction a first web of material having a medial portion thereof;

a second supplying means which provides a second web of release material along the machine direction;

first assembling means for attaching the second web of release material to said medial portion of said first web along said machine-direction to provide a web laminate;

first parting means for separating said web laminate into at least a first laminate section and a second laminate section, each laminate section including a portion of said first web and a portion of said second web of release material, and each laminate section having an edge region thereof;

directing means for spacing apart said first and second laminate sections;

delivering means which locates a securement web between said first and second laminate sections, where said securement web has a first side region a second side region, and a securing means on a securing surface of the securement web;

second assembling means for affixing said edge region of said first laminate section to said first side region of said securement web, and affixing said edge region of said second laminate section to said second side region of said securement web to thereby form a composite base web which has a medial portion thereof; and second parting means for dividing said composite web along its medial portion to form at least a first composite securement web and a second composite securement web.

12. An apparatus as recited in claim 11, further comprising means for sectioning said first and second composite securement webs to provide a plurality of individual fastener systems.

13. An apparatus as recited in claim 11, wherein said supplying means provides said first web in a form which is elastically stretchable at least along a cross-direction of said first web.

14. An apparatus as recited in claim 11, wherein
said delivering means provides said securement web in a form which includes an adhesive fastening material on a major facing surface of said securement web.

15. An apparatus as recited in claim 11, wherein said delivering means provides said securement web in a form which includes a hook component of a hook-and-loop fastening system on a major facing surface of said securement web.

16. An apparatus as recited in claim 11, wherein said delivering means provides said securement web in a form which includes a loop component of a hook-and-loop fastening system on a major facing surface of said securement web.

17. An apparatus as recited in claim 12, further comprising means for folding said first and second composite securement webs to provide first and second folded composite webs.

18. An apparatus as recited in claim 12, further comprising:

means for affixing said individual fasteners to opposed sides of an article web, means for substantially aligning opposed pairs of said individual fasteners along a cross-direction of said article web, and means for separating said article web into a plurality of individual articles.

19. An apparatus as recited in claim 11, wherein said second parting means is arranged for dividing said composite web along a serpentine line which extends into said first and second laminate sections.

* * * * *